United States Patent [19]

Dosmann

[11] Patent Number: 5,477,326
[45] Date of Patent: Dec. 19, 1995

[54] SPECTROPHOTOMETER ARRANGEMENT WITH MULTI-DETECTOR READHEAD

[75] Inventor: Andrew J. Dosmann, Granger, Ind.

[73] Assignee: Bayer Corporation, Elkhart, Ind.

[21] Appl. No.: 269,363

[22] Filed: Jun. 30, 1994

[51] Int. Cl.$^6$ .................................................. G01N 21/25
[52] U.S. Cl. ........................ 356/406; 356/407; 356/409; 250/226
[58] Field of Search .................................. 356/402, 405, 356/406, 407, 409, 414, 416, 419, 425; 250/226; 257/80, 84, 88, 89, 440

[56] References Cited

U.S. PATENT DOCUMENTS 4,834,541  5/1989  Yamaba .................................. 356/407

FOREIGN PATENT DOCUMENTS 3444104  6/1986  Germany .............................. 356/402

OTHER PUBLICATIONS

Mims III, Forest M., "Sun Photometer With Light–Emitting Diodes As Spectrally Selective Detectors", *Applied Optics*, vol. 31, No. 33, Nov. 20, 1992.

*Primary Examiner*—F. L. Evans
*Attorney, Agent, or Firm*—Jerome L. Jeffers

[57] ABSTRACT

A photometer readhead is used to measure concentrations within a test sample of preselected color-developed analytes having different characteristic absorption bands. The photometer readhead comprises an artificial light source for illuminating the test sample, a plurality of light-emitting diodes for detecting light transmitted through or reflected from the test sample, and a housing assembly for enclosing and supporting the plurality of light-emitting diodes. The plurality of light-emitting diodes have spectral responses encompassing respective ones of the different characteristic absorption bands of the preselected color-developed analytes. The plurality of light-emitting diodes preferably include a first light-emitting diode having a spectral response in red portion of the visible light spectrum; a second light-emitting diode having a spectral response in the blue portion of the visible light spectrum, a third light-emitting diode having a spectral response in the green portion of the visible light spectrum, and a fourth light-emitting diode having a spectral response in the infrared light spectrum.

14 Claims, 2 Drawing Sheets

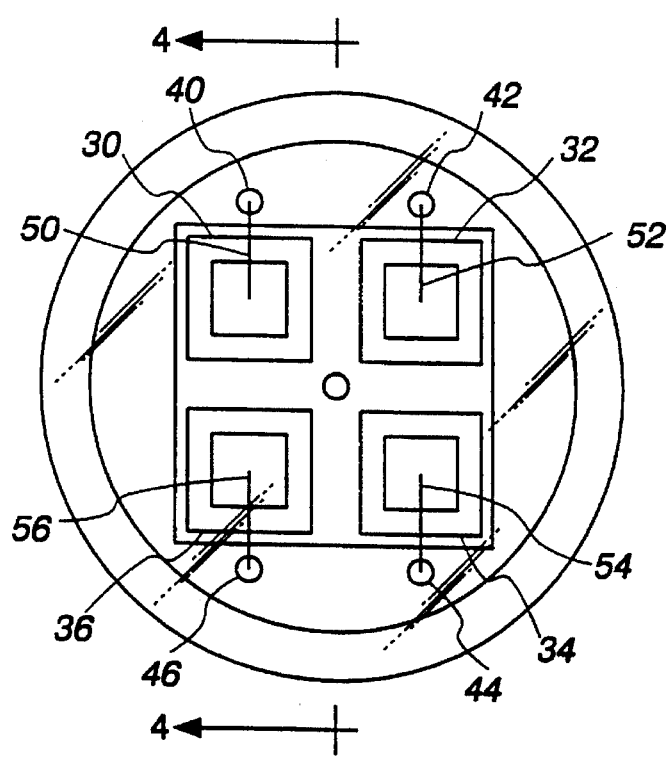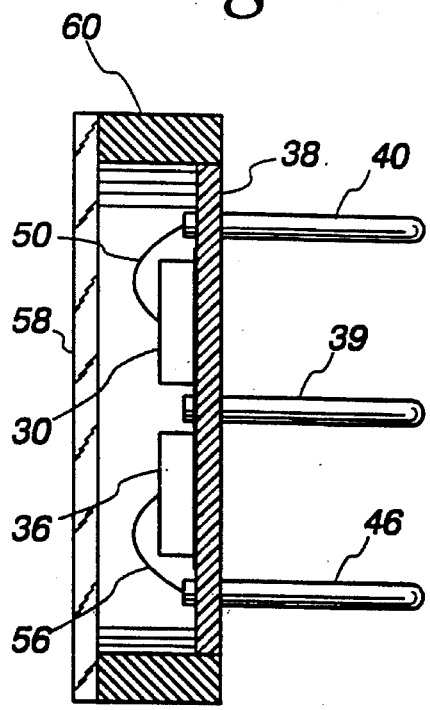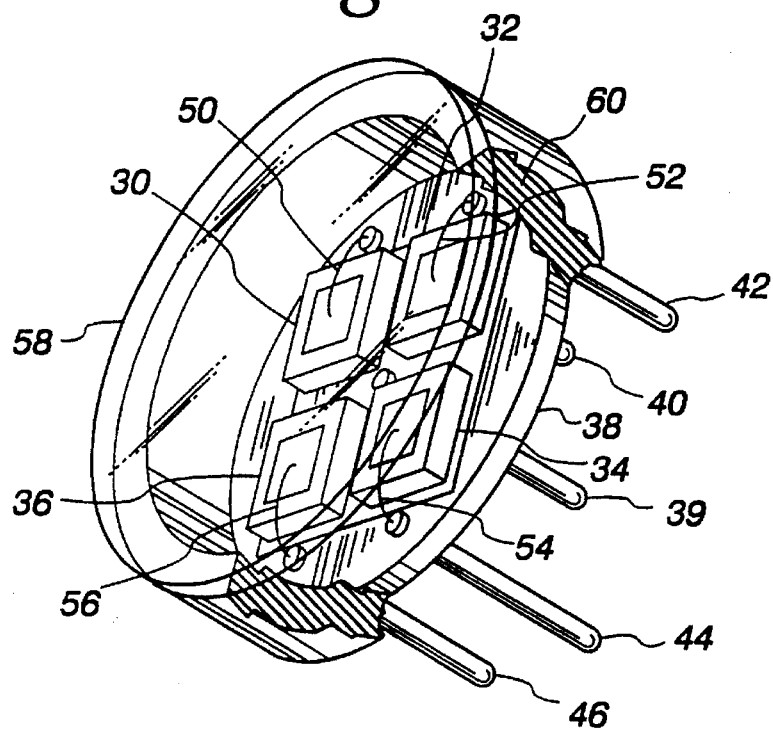

SPECTROPHOTOMETER ARRANGEMENT WITH MULTI-DETECTOR READHEAD

FIELD OF THE INVENTION

The present invention relates generally to photometers used for reflectance and transmittance applications and, more particularly, relates to a multi-detector photometer readhead which uses light-emitting diodes (LEDs) to simultaneously detect light from color-developed analytes in a test sample.

BACKGROUND OF THE INVENTION

Photometer readheads with a plurality of detectors are commonly used for quantitative chemical analysis, such as analysis of body fluids. A known quantity of body fluid sample, such as blood or urine, is placed on a test strip or in a test tube containing reagents which react with one or more quantitatively unknown body fluid components (analytes) to develop color in the analytes. Typical analytes of interest for urine include glucose, blood, bilirubin, urobilinogen, nitrite, protein, and ketone bodies. After adding color-developing reagents to urine, the foregoing analytes of interest have the following colors: glucose is bluish green; bilirubin, urobilinogen, nitrite, and ketone bodies are green; and blood and protein are red. The color developed in a particular analyte defines the characteristic discrete spectrum for absorption of light for that particular analyte. For example, the characteristic absorption spectrum for color-developed glucose falls within the upper end of the blue spectrum and the lower end of the green spectrum.

After adding reagents to develop color in the analytes of interest, an artificial source of controlled, diffuse light having a broad spectral output illuminates the test sample. The light reflected from or transmitted through the test sample is detected simultaneously by the plurality of detectors. The detectors are configured to detect different bands of wavelengths with each band containing those wavelengths which would be absorbed by one of the color-developed analytes, if present, in the test sample. That is, the spectral response of each detector encompasses the characteristic discrete spectrum of wavelengths for absorption of light of a particular color-developed analyte. The degree of absorption of light by that particular analyte is proportional to the concentration of the particular analyte in the test sample. This means that the amount of light reflected from or transmitted through the color-developed analyte to its corresponding detector is inversely proportional to the concentration of the analyte in the test sample. As a result, the concentration of the different color-developed analytes is determined by measuring the intensity of light sensed by the different detectors.

The detectors are typically silicon photodetectors having a broad band spectral response covering the range of wavelengths between 300 nm and 1100 nm. To limit the spectral responses of the silicon photodetectors to different wavelength bands, a different optical filter is positioned in front of each silicon photodetector. For example, a green optical filter is positioned in front of a first silicon photodetector, a blue optical filter is positioned in front of a second photodetector, and a red optical filter is positioned in front of a third photodetector. Thus, the silicon photodetectors are accompanied by respective optical filters with each optical filter transmitting a different band of wavelengths to its corresponding detector. Furthermore, using a specially designed housing assembly, the filter and photodetector combinations are optically isolated from each other to prevent optical crosstalk between the combinations. Optical crosstalk occurs when light passing through the optical filter and entering the photodetector of one filter and photodetector combination also enters the photodetector of another filter and photodetector combination. Since the concentration of a specific analyte is determined by the amount of light detected by the filter and photodetector combination targeting that analyte, optical crosstalk will decrease the accuracy of that determination. To optically isolate the filter and photodetector combinations from each other, the housing assembly containing these combinations includes partitions between these combinations which are impervious to light.

A drawback of using silicon photodetectors combined with optical filters to limit the spectral responses of the photodetectors is that the housing assembly containing the filter and photodetector combinations is relatively bulky. First, the housing assembly must accommodate the optical filters by securing the filters in the assembly and locating the filters in front of their respective photodetectors. Second, the housing assembly must accommodate the optically impervious partitions for optically isolating the filter and photodetector combinations from each other. A related drawback of using filter and photodetector combinations is that the component and assembly costs are relatively high. Each filter and photodetector combination is relatively expensive, and it is costly and difficult to manufacture the housing assembly for mounting these combinations and preventing optical crosstalk therebetween.

Another drawback of using filter and photodetector combinations is that the optical filters still transmit wavelengths, albeit attenuated wavelengths, outside the passband. If the spectral responses of the combinations overlap with each other, the accuracy of the measured concentrations of the different analytes targeted by the combinations is reduced. For most accurate calculations of analyte concentration, it is preferable to strictly confine the spectral responses of the photodetectors to the respective characteristic absorption bands of the color-developed analytes without the spectral responses overlapping each other.

A need therefore exists for a multi-detector readhead of a photometer for reflectance and transmittance applications which overcomes the aforementioned shortcomings associated with existing photometers using filter and silicon photodetector combinations for light detection.

SUMMARY OF THE INVENTION

Accordingly, an object of the present invention is to provide a multi-detector readhead of a photometer for reflectance and transmittance applications which enhances optical isolation between the detectors and, at the same time, is relatively compact in design.

Another object of the present invention is to provide a multi-detector readhead which is cost-effective and easy to manufacture.

In a particular embodiment the foregoing objects are realized by providing a multi-detector readhead for measuring concentrations within a test sample of preselected color-developed analytes having different characteristic absorption bands. The readhead comprises an artificial light source for illuminating the test sample, a plurality of light-emitting diodes for detecting light reflected from or transmitted through the sample, and a housing assembly for supporting the plurality of light-emitting diodes. The light-emitting diodes are configured to function as spectrally selective detectors with different spectral responses. The spectral response of one of the light-emitting diodes is preferably outside the characteristic absorption bands of the reaction products within the sample, while the spectral responses of the remaining light-emitting diodes encompass respective ones of the characteristic absorption bands of the color-developed analytes. In a reflectance photometer, the plurality of light-emitting diodes are disposed on the same side of the test sample as the light source so that the light-emitting diodes detect light reflected from the test sample. In a transmittance photometer, the plurality of light-emitting diodes are disposed on the opposite side of the test sample relative to the light source so that the light-emitting diodes detect light transmitted through the test sample.

The light-emitting diodes have different spectral responses with virtually no overlap so as to inherently provide optical isolation between the light-emitting diodes. Therefore, no optical filters are necessary to limit the spectral responses of the light-emitting diodes, and the housing assembly need not be specially designed with partitions to prevent optical crosstalk between the light-emitting diodes. Without the need for optical filters or a specially designed housing assembly, the photometer readhead of the present invention is less expensive than the prior art readhead and is easier to manufacture. In addition, since the housing assembly need not accommodate optical filters or optically impervious partitions, the housing assembly of the present invention is more compact than the housing assembly employed with the prior art readhead.

BRIEF DESCRIPTION OF THE DRAWINGS

Other objects and advantages of the invention will become apparent upon reading the following detailed description and upon reference to the drawings in which:

FIG. 3 is a plan view of a detector assembly employed with the readheads in FIGS. 1–2;

FIG. 4 is a section taken generally along the line 4—4 in FIG. 3; and

FIG. 5 is a perspective view of the detector assembly in FIGS. 3–4.

Figure 1:
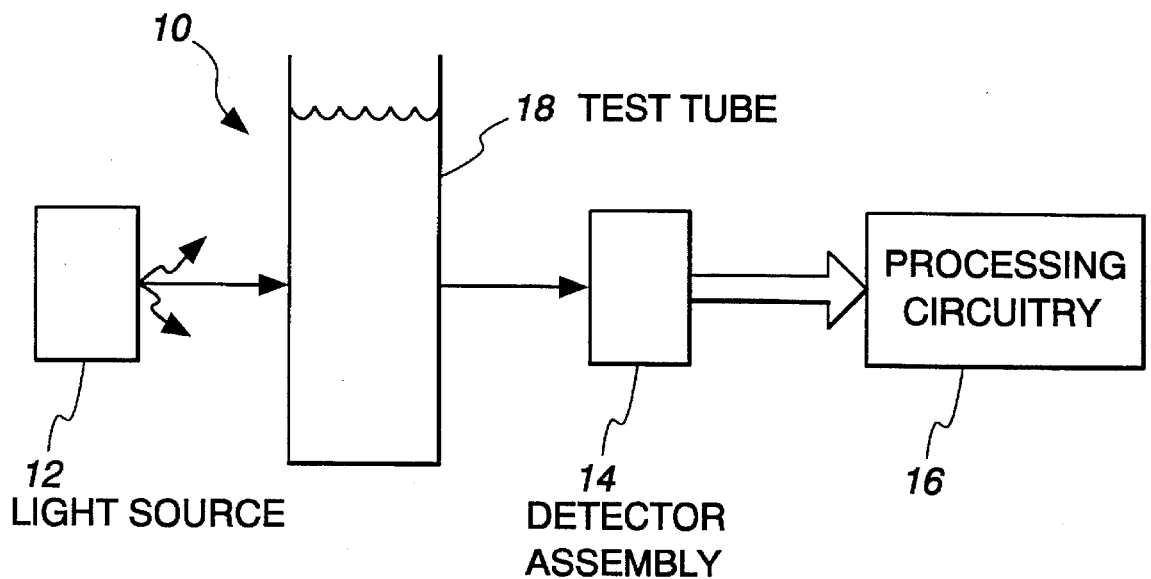
FIG. 1 is a diagrammatic side view of a readhead for a transmittance photometer in accordance with the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

Turning now to the drawings, FIG. 1 illustrates a readhead 10 for a transmittance photometer having an artificial light source 12, a detector assembly 14, and processing circuitry 16. The light source 12 preferably emits controlled, diffuse light having a broad spectral output. Examples of such artificial light sources meeting these criteria include incandescent, halogen, or fluorescent lamps. Alternatively, the light source 12 may be a plurality of light-emitting diodes having different spectral emission bands. The light produced by the light source 12 impinges on a test tube or vial 18 containing a body fluid sample. Reagents have been added to the body fluid sample to develop color in the analytes of interest. As the light travels through the test sample, the light is absorbed to varying degrees and transmitted in a scattered pattern. Some of the transmitted light is detected by the detector assembly 14, which is disposed on the opposite side of the fluid sample relative to the light source 12. The detector assembly 14 includes a plurality of detectors with different spectral responses for detecting the light transmitted through the mixture. One of the detectors preferably has a spectral response outside the characteristic absorption bands of the color-developed analytes within the test sample so that the detector senses light without absorption. The amount of light detected by this detector represents a reference value against which the light detected by the other detectors may be compared to determine the degree of absorption. These other detectors sense different bands of wavelengths with each band covering the characteristic absorption band of a corresponding color-developed analyte. Each detector of the detector assembly 14 converts the light (photons) detected by that detector into an electrical output signal which is transmitted to the processing circuitry 16. The processing circuitry 16 determines the concentrations of the color-developed analytes based on the amount of light detected by each detector.

Figure 2:
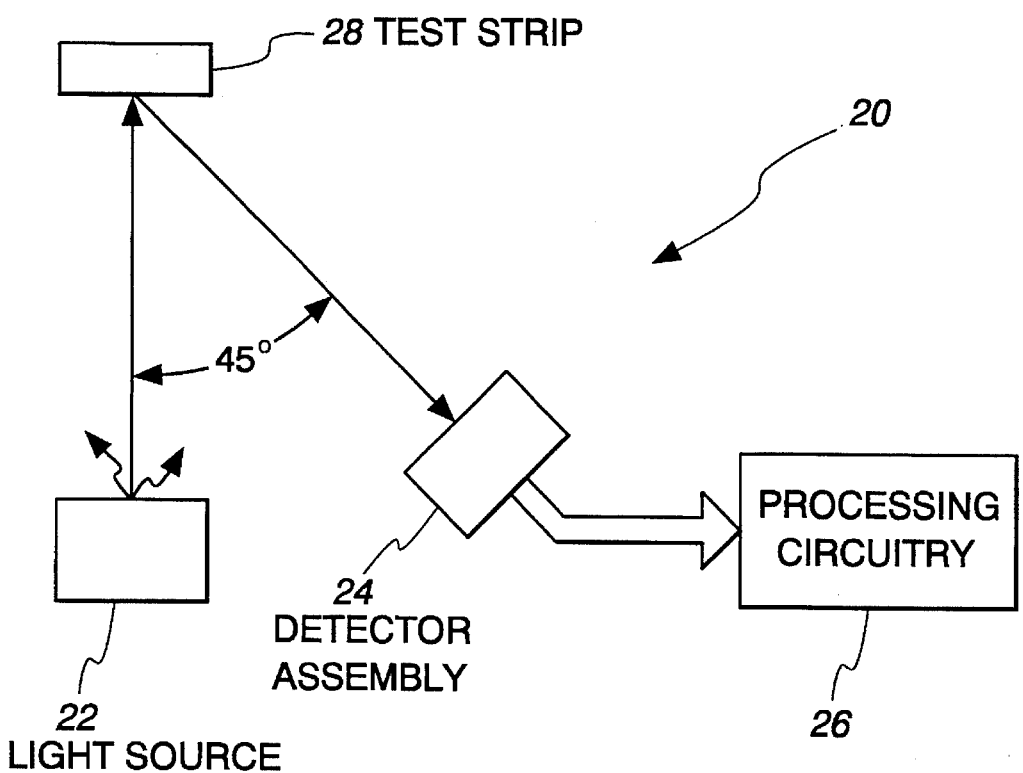
FIG. 2 is a diagrammatic side view of a readhead for a reflectance photometer in accordance with present invention.

FIG. 2 illustrates a typical geometrical arrangement for a readhead 20 of a reflectance photometer. The readhead 20 includes an artificial light source 22, a detector assembly 24, and processing circuitry 26. Like the light source 12, the light source 22 preferably generates controlled, diffuse light having a broad spectral output. Alternatively, the light source 22 is a plurality of light-emitting diodes having different spectral emission bands. The light source 22 illuminates a body fluid sample on a test strip or pad impregnated with reagents. The reagents react with analytes of interest within the body fluid sample to develop color in the analytes. Light striking the test strip 28 is a absorbed to varying degrees and reflected in a scattered pattern. Some of the reflected light is detected by the detector assembly 24. Like the detector assembly 14; the detector assembly 24 includes a plurality of detectors for detecting different wavelength bands. One of the wavelength bands is outside the characteristic absorption bands of the color-developed-analytes to generate a reference value. The remaining wavelength bands each encompass the characteristic absorption band of a corresponding color-developed analyte so that the amount of light sensed by the detectors with these remaining wavelength bands is proportional to the concentrations of the analytes of interest. These concentrations are calculated by transmitting the electrical output signals produced by the different detectors of the detector assembly 24 to the processing circuitry 26.

Since the readhead 20 is used for reflectance applications, the detector assembly 24 is disposed on the same side of the test strip 28 as the light source 22. In the preferred embodiment, the light source 22 is mounted in the readhead 20 perpendicular to the test strip 28. The detector assembly 24 is mounted at a scattering angle of 45 degrees as measured between a line representing the direction of travel of the incoming light from the light source 22 to the test strip 28 and a line representing the direction of travel of the reflected light from the test strip 28 to the detector assembly 24. While other scattering angles may be used, it is well-known in the art that a scattering angle of 45 degrees is most efficient.

The detector assemblies 14, 24 in FIGS. 1–2 are preferably constructed as depicted in FIGS. 3–5. Each detector assembly includes a plurality of light-emitting diodes 30, 32, 34, and 36 mounted to a printed circuit board 38. The cathodes of these light-emitting diodes are disposed adjacent the printed circuit board 38 and are connected a ground plane on the circuit board 38 using solder, conductive paste, or the like. To ground the cathodes a grounding wire 39 extends through the printed circuit board 38 and is connected to the ground plane. The anodes of the light-emitting diodes 30, 32, 34, and 36 are disposed opposite the cathodes and are coupled to respective lead wires 40, 42, 44, and 46 by means of respective bond wires 50, 52, 54, and 56. At one end, the lead wires 40, 42, 44, and 46 extend through the printed circuit board 38 and are electrically insulated from the ground plane formed thereon. At the other end, the lead wires 40, 42, 44, and 46 are connected to processing circuitry (see FIGS. 1–2) disposed on a motherboard. In the foregoing manner, the light-emitting diodes 30, 32, 34, and 36 are configured to function as detectors, instead of emitters. In an alternative embodiment, the printed circuit board 38 is replaced with a metal plate (e.g., brass plate) so that the grounding wire 39 and the cathodes of the light-emitting diodes 30, 32, 34, and 36 are simply connected to any part of the plate for grounding. To prevent grounding of the lead wires 40, 42, 44, and 46 as they pass through the plate, the lead wires are insulated from the plate at those locations where they pass through the plate.

To isolate the light-emitting diodes 30, 32, 34, and 36 from environmental effects such as humidity and to prevent contamination of the die composition forming the light-emitting diodes 30, 32, 34, and 36, the light-emitting diodes are enclosed within a cylindrical housing having a transparent cover or window 58, a base corresponding to the printed circuit board 38, and a cylindrical side wall 60 bridging the window 58 and the printed circuit board 38. To permit light energy from the test sample to freely enter the housing, the window 58 is preferably composed of glass or plastic. To concentrate the light energy as it enters the housing, the window 58 may be configured in the shape of a lens. The cylindrical side wall 60 of the housing is preferably composed of metal or plastic and, if composed of metal, may be connected to the circular edge of the printed ,circuit board 38 by spot welding.

Serving as light detectors, each of the light-emitting diodes 30, 32, 34, and 36 has a narrow spectral response which permits the diode to detect only a narrow band of wavelengths. The detected wavelength band is determined by the die composition of the light-emitting diode. In accordance with tests performed by the present inventor, Table 1 lists the typical spectral response characteristics of light-emitting diodes having different die compositions:

| Die Composition | Peak Wavelength | Response Bandwidth at FWHM |
| --- | --- | --- |
| GaAs | 910 nm | 170 nm |
| GaAlAs | 840 nm | 50 nm |
| GaAlAs | 680 nm | 150 |
| GaAlAs | 670 nm | 165 |
| GaP | 520 nm | 90 |

The "Peak Wavelength" is the wavelength corresponding to the maximum response (in amperes per watt) of the light-emitting diode. The "Response Bandwidth at FWHM" is the full width, in terms of wavelength, of a spectral response curve at half the maximum response. In other words, the "Response Bandwidth at FWHM" is the difference between the wavelengths on both sides of a spectral response curve at which the response quantity reaches half its maximum intensity.

It can be seen from Table 1 that the spectral responses of the first and second entries substantially fall within the infrared spectrum, the spectral responses of the third and fourth entries substantially fall within the red spectrum, and the spectral response of the fifth entry substantially falls within the green spectrum. Furthermore, the response bandwidths of the tested light-emitting diodes range from approximately 50 nm to approximately 170 nm. In addition to the tested light-emitting diodes, light-emitting diodes with spectral responses falling within other portions of the light spectrum or with response bandwidths smaller than 50 nm may be employed for the present invention.

The three light-emitting diodes 30, 32, and 34 in FIGS. 3–5 are selected such that their spectral responses are substantially distinct from each other. Moreover, the light-emitting diodes 30, 32, and 34 are selected such that their spectral responses encompass the characteristic discrete spectrums for absorption of light of three different color-developed analytes (formed from analytes of interest) having three non-overlapping characteristic absorption bands. For any given test, the concentrations of three different color-developed analytes having substantially non-overlapping absorption bands may be determined. For example, if reagents develop the color red for analyte A, blue for analyte B, and green for analyte C, the characteristic absorption bands of analytes A, B, and C are located within the respective red, blue, and green portions of the visible light spectrum. Therefore, the light-emitting diodes 30, 32, 34 are selected such that their spectral responses do not overlap with each other and such that their spectral responses encompass the respective characteristic absorption bands of analytes A, B, and C. In this example, the light-emitting diode 30 would be "red" light-emitting diode, the light-emitting diode 32 would be a "blue" light-emitting diode, and the light-emitting diode 34 would be a "green" light-emitting diode.

The fourth light-emitting diode 36 is preferably selected such that its spectral response does not contain the characteristic absorption spectrums of the color-developed analytes. In the preferred embodiment, this light-emitting diode 36 has a spectral response in the infrared spectrum because none of the color-developed analytes has a characteristic absorption band in this portion of the light spectrum. The amount of light received by the light-emitting diode 36 is not affected by the concentration of the analytes of interest within the body fluid sample. Therefore, the amount of light detected by the infrared light-emitting diode 36 establishes a reference value corresponding to negligible absorption of light. Using processing circuitry (see the processing circuitry 16, 26 in FIGS. 1–2), the amount of light detected by the other three light-emitting diodes 30, 32, and 34 is compared to this reference value to determine the amount of light absorbed by the respective color-developed analytes, thereby determining the concentrations of the analytes.

A significant advantage of using the light-emitting diodes as detectors, as opposed to the filter and photodetector combinations of the prior art, is that the light-emitting diodes inherently provide optical isolation between each other because they reject wavelengths outside their spectral responses. This inherent optical isolation means not only that optical filters are not necessary to limit the spectral responses of the light-emitting diodes, but also that the housing need not include partitions to optically isolate the light-emitting diodes from each other. Without the optical filters and the housing partitions, the detector assembly (and the photometer readhead) of the present invention is more compact, less costly, and easier to manufacture than the prior art detector assembly and readhead. The compactness of the detector assembly also results from the light-emitting diodes being much smaller in width than the filter and photodetector combinations used in the prior art readhead. In the preferred embodiment, the diameter of the cylindrical housing is approximately 0.04 inches and the width of each light-emitting diode is approximately 0.01 inches. In contrast, the housing assembly for housing the filter and photodetector combinations of the prior art has an approximate width of 0.40 inches and the width of each combination is 0.08 inches or more. It should be apparent that the detector assembly illustrated in FIGS. 3–5 is substantially more compact than the detector assembly employed with the prior art filter and photodetector combinations. Due to the simple construction of the housing and the fact that the light-emitting diodes are significantly less expensive than the filter and photodetector combinations of the prior art, the detector assembly in FIGS. 3–5 is more cost-effective than the detector assembly used in the prior art readhead.

Another important advantage of using the light-emitting diodes, as opposed to the filter and photodetector combinations, is that the spectral responses of the light-emitting diodes are more discrete than the spectral responses of the filter and photodetector combinations of the prior art. As a result, the spectral response of each light-emitting diode is strictly confined to the characteristic absorption band of its corresponding color-developed analyte. Since the spectral responses of the light-emitting diodes do not overlap with each other, the concentrations of the analytes of interest in the test sample are measured with a high degree of accuracy.

In addition to implementing the detector assemblies with the light-emitting diodes 30, 32, 34, and 36, the light sources 12, 22 may also be implemented with light-emitting diodes to further reduce the cost of the readhead and reduce power consumption of the light sources 22. The number of light-emitting diodes in the light source is equal to the number of light-emitting diodes in the detector assembly. Therefore, if the detector assembly includes the four light-emitting diodes 30, 32, 34, and 36, the light source would include four light-emitting diodes. The light-emitting diodes in the light source are selected so that their spectral emission bands are associated with the spectral responses of the light-emitting diodes 30, 32, 34, and 36 of the detector assembly. This results in the creation of several unique spectral bandpasses.

While the present invention has been described with reference to one or more particular embodiments, those skilled in the art will recognize that many changes may be made thereto without departing from the spirit and scope of the present invention. For example, the detector assembly in FIGS. 3–5 may be modified to include more or less than four light-emitting diodes. Furthermore, the infrared light-emitting diode 36 used for establishing a reference value indicative of negligible light absorption may be removed from the detector assembly. In this case, the reference value is established using another detector assembly which receives light directly from the light source, without the light first being reflected from or transmitted though the test sample. Each of these embodiments and obvious variations thereof is contemplated as falling within the spirit and scope of the claimed invention, which is set forth in the following claims.

What is claimed is:

1. A spectrophotometer arrangement, comprising:

a biological test sample containing unknown concentrations of preselected color-developed analytes having different characteristic absorption bands;

an artificial light source for illuminating the biological test sample;

a plurality of light-emitting diodes for detecting light from the biological test sample, said plurality of light-emitting diodes having spectral responses encompassing respective ones of the different characteristic absorption bands of the preselected color-developed analytes; and a housing assembly for supporting said plurality of light-emitting diodes, wherein said housing assembly includes a base and said plurality of light-emitting diodes are mounted to said base, and wherein said housing assembly includes a window disposed opposite said base and a side wall bridging said base and said window such that said plurality of light-emitting diodes are enclosed within said housing assembly.

2. The photometer readhead of claim 1, wherein said plurality of light-emitting diodes are disposed on an opposite side of the test sample relative to said artificial light source so that said plurality of light-emitting diodes detect a portion of light transmitted through the test sample.

3. The photometer readhead of claim 2, wherein said artificial light source, the test sample, and said plurality of light-emitting diodes are disposed in line with each other.

4. The photometer readhead of claim 1, wherein said plurality of light-emitting diodes are disposed on the same side of the test sample as said artificial light source so that said plurality of light-emitting diodes detect a portion of light reflected from the test sample.

5. The photometer readhead of claim 4, wherein said plurality of light-emitting diodes are disposed at a scattering angle of approximately 45 degrees as measured between a line representing a direction of travel of light from said artificial light source to the test sample and a line representing a direction of travel of the reflected light portion from the test sample to said plurality of light-emitting diodes.

6. The photometer readhead of claim 1, wherein said artificial light source is selected from the group consisting of an incandescent lamp, a halogen lamp, a fluorescent lamp, and a plurality of light-emitting diodes.

7. The photometer readhead of claim 1, wherein said plurality of light-emitting diodes include a first light-emitting diode having a spectral response in the red portion of the visible light spectrum, a second light-emitting diode having a spectral response in the blue portion of the visible light spectrum, and a third light-emitting diode having a spectral response in the green portion of the visible light spectrum.

8. The photometer readhead of claim 7, wherein said plurality of light-emitting diodes include a fourth light-emitting diode having a spectral response in the infrared light spectrum.

9. The photometer readhead of claim 1, wherein said base includes a printed circuit board.

10. A spectrophotometer arrangement, comprising:

a biological test sample containing unknown concentrations of preselected color-developed analytes having different characteristic absorption bands;

an artificial light source for illuminating the biological test sample; and a detector assembly for detecting light from the biological test sample, said detector assembly including a plurality of light-emitting diodes having spectral responses encompassing respective ones of the different characteristic absorption bands of the preselected color-developed analytes, said plurality of light-emitting diodes including a pair of light-emitting diodes having respective spectral responses in different portions of the visible light spectrum such that said respective spectral responses are substantially non-overlapping;

wherein said detector assembly includes a housing for enclosing and supporting said plurality of light-emitting diodes and wherein said housing includes a base and said plurality of light-emitting diodes are mounted to said base, and wherein said housing includes a window disposed opposite said base and a side wall bridging said base and said window such that said plurality of light-emitting diodes are enclosed within said housing; and wherein said plurality of light-emitting diodes are disposed at a scattering angle of approximately 45 degrees as measured between a line representing a direction of travel of light from said artificial light source to the test sample and a line representing a direction of travel of the reflected light portion from the test sample to said plurality of light-emitting diodes.

11. The photometer readhead of claim 10, wherein a first of said pair of light-emitting diodes has a spectral response in the red portion of the visible light spectrum and a second of said pair of light-emitting diodes has a spectral response in the blue portion of the visible light spectrum, and wherein said plurality of light-emitting diodes includes a third light-emitting diode having a spectral response in the green portion of the visible light spectrum.

12. The photometer readhead of claim 11, wherein said plurality of light-emitting diodes include a fourth light-emitting diode having a spectral response in the infrared light spectrum.

13. The photometer readhead of claim 10, wherein said base includes a printed circuit board.

14. The photometer readhead of claim 10, wherein said artificial light source is selected from the group consisting of an incandescent lamp, a halogen lamp, a fluorescent lamp, and a plurality of light-emitting diodes.

\* \* \* \* \*